(12) United States Patent
Maier

(10) Patent No.: US 6,671,629 B2
(45) Date of Patent: Dec. 30, 2003

(54) METHOD AND DEVICE FOR MEASURING CHARACTERISTICS OF A SAMPLE

(75) Inventor: Peter Maier, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/171,964

(22) Filed: Jun. 17, 2002

(65) Prior Publication Data

US 2003/0028329 A1 Feb. 6, 2003

Related U.S. Application Data

(63) Continuation of application No. PCT/DE00/04456, filed on Dec. 14, 2000.

(30) Foreign Application Priority Data

Dec. 15, 1999 (DE) .......................... 199 60 586

(51) Int. Cl.$^7$ .............................................. G06F 3/00
(52) U.S. Cl. .......................... 702/28; 702/27; 702/32; 702/69
(58) Field of Search ......................... 702/27, 28, 32, 702/69, 76, 134, 172; 600/318; 250/573; 435/174; 356/369

(56) References Cited

U.S. PATENT DOCUMENTS

| | | | |
|---|---|---|---|
| 4,155,009 A | 5/1979 | Lieber et al. ............... 250/308 |
| 5,576,544 A | 11/1996 | Rosenthal ................. 250/341.1 |
| 5,872,630 A | * 2/1999 | Johs et al. ................... 356/369 |
| 6,198,532 B1 | * 3/2001 | Cabib et al. ................ 356/346 |
| 6,280,381 B1 | * 8/2001 | Malin et al. ................ 600/322 |
| 6,441,388 B1 | * 8/2002 | Thomas et al. ............. 250/573 |

OTHER PUBLICATIONS

H. Mark, "Principles and Practice of Spectroscopic Calibration" in Chemical Analysis, 1991, pp 85–147, vol. 118, John Wiley & Sons, Inc., New York.

* cited by examiner

*Primary Examiner*—Marc S. Hoff
*Assistant Examiner*—Felix Suarez
(74) *Attorney, Agent, or Firm*—Sughrue Mion, PLLC

(57) ABSTRACT

A method and a device for measuring the characteristics of a sample by spectral analysis. According to the method, the characteristics are calculated from the spectral data obtained by the spectral analysis, using a calibration model that has been established on the basis of reference samples. In order to improve the stability of the measuring process, an additional calculation of the characteristics (16) of the samples (1) takes place, using at least one additional calibration model (14) that has been established on the basis of additional reference samples (1"). Deviations between the characteristics (12, 16) calculated by the respective calibration models (11, 14) are determined and output.

18 Claims, 1 Drawing Sheet

2..........spectrometer
4..........radiation source
5..........monochromator
7..........measuring cell
9..........detector
11........calibration model
14........additional calibration model
17........comparator
19........selection unit

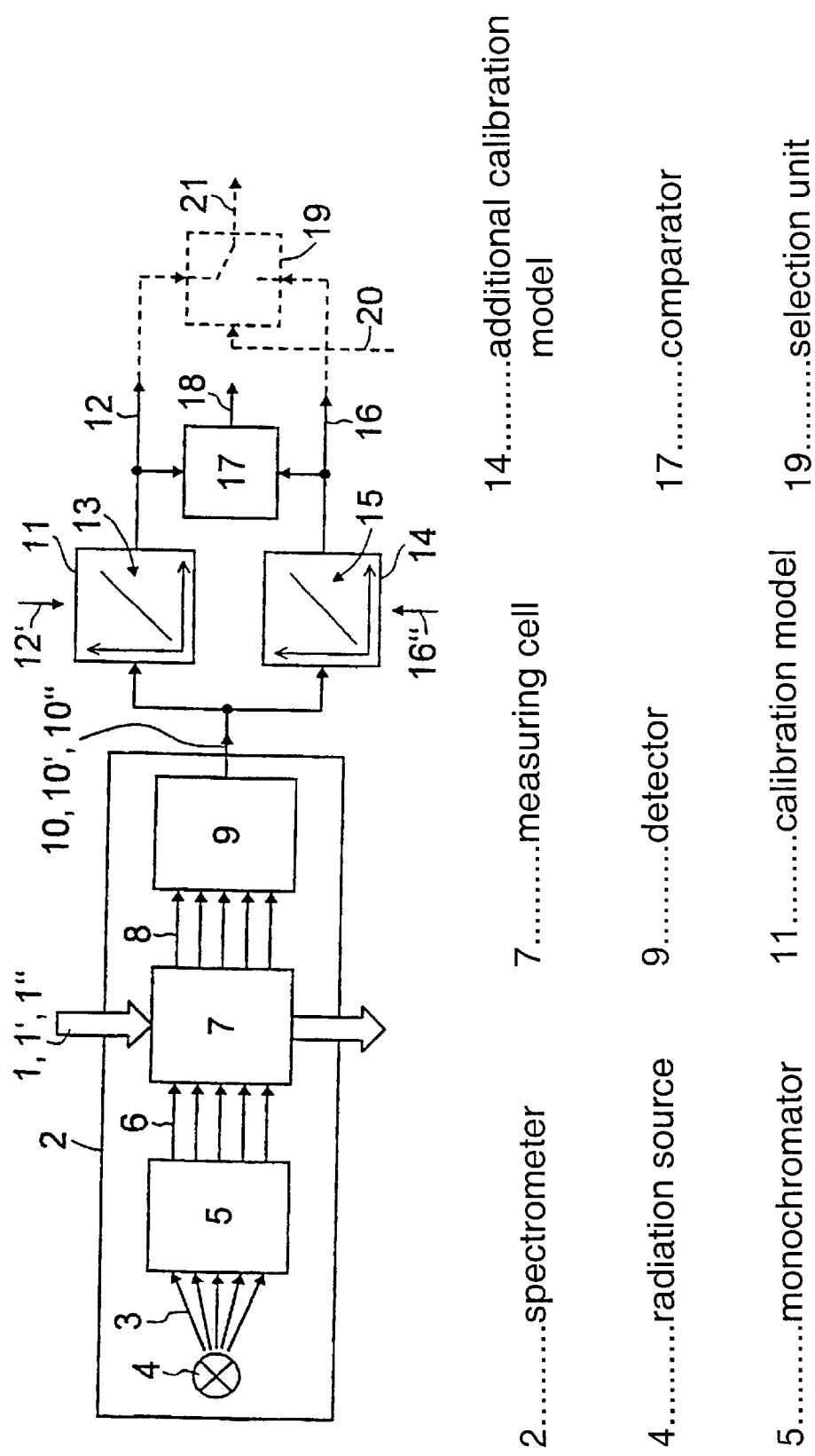

METHOD AND DEVICE FOR MEASURING CHARACTERISTICS OF A SAMPLE

This is a Continuation of International Application PCT/DE00/04456, with an international filing date of Dec. 14, 2000, which was published under PCT Article 21(2) in German, and the disclosure of which is incorporated into this application by reference.

FIELD OF AND BACKGROUND OF THE INVENTION

The invention relates to a method for measuring the characteristics of a sample by spectral analysis. The spectral data thus obtained are used to calculate the characteristics by way of a calibration model that has been established on the basis of reference samples.

The invention further relates to a device for measuring the characteristics of a sample using a spectrometer for spectral analysis of the sample and a calibration model that has been established on the basis of reference samples and that calculates the characteristics from the spectral data delivered by the spectrometer.

One example of spectral analysis of samples is NIR spectroscopy, in which the molecular structure in the sample material is excited by photons in the near infrared range (NIR). The molecules reach vibration states corresponding to their structure and exhibit typical energy absorptions. In the resulting spectrum, the energy absorption values are recorded relative to discrete wavelengths by means of a detector. The characteristics of the sample to be determined are then calculated from the spectral data thus obtained using a calibration model.

These characteristics can in principle comprise all the sample parameters that correlate with the information content of the spectrum. Thus, the characteristics include, in particular, the molecular structure of the sample and the physical and chemical properties resulting therefrom. The calibration model is established by chemometric methods, such as MLR (Multiple Linear Regression) or PLS (Partial Least Squares) on the basis of the spectral data and the characteristics of selected or prepared reference samples. The characteristics of the reference samples are already known and/or are determined by reference analysis, for example in the laboratory. The reference samples must correspond as far as possible with the respective samples to be analyzed and cover, representatively, the range in variations of the characteristics of the sample to be determined.

In practice, it is difficult to ensure that the measurements of certain characteristics of samples performed by means of the calibration model, once established, remain accurate as long as possible. Over time, there may be changes in the measuring device or in the sample composition that go unnoticed. Furthermore, there may always be influences that failed to be taken into account when the calibration model was established, e.g., due to the selection of the reference samples or due to the external circumstances of calibration. This can lead to increased measuring errors. The calibration model must therefore be checked within the context of control measurements at certain time intervals or by means of random calibration checks whenever the external conditions change. If the measurement deviation is too large, the existing calibration model must be recalibrated or corrected.

OBJECTS OF THE INVENTION

An object of the invention is automatically to detect with the least possible effort any measurement deviations even before a check measurement, and to identify the sample affected.

SUMMARY OF THE INVENTION

This and other objects are attained by the invention in its various formulations. According to one formulation, the invention is directed to a method for measuring characteristics of a sample by spectral analysis, which includes: calculating the characteristics from spectral data obtained from the spectral analysis using a calibration model that has been established on the basis of reference samples; performing an additional calculation of the characteristics of the sample based on the same spectral data using at least one additional calibration model that has been established on the basis of additional reference samples; and determining and outputting deviations between the characteristics calculated by the respective calibration models, to permit an evaluation of the quality of the measurement.

According to another formulation, the invention is directed to a device for measuring characteristics of a sample, which includes: a spectrometer for spectral analysis of the sample; a calibration model that has been established on the basis of reference samples and that calculates the characteristics from spectral data supplied by the spectrometer; at least one additional calibration model that has been established on the basis of additional reference samples and that performs an additional calculation of the characteristics; and a comparator arranged downstream from the calibration models, which determines deviations between the characteristics calculated by the respective calibration models.

As such, in the above-summarized method, at least one additional calibration model is established on the basis of additional reference samples. This additional calibration model is then used for an additional calculation of the characteristics of the sample. Any deviations between the characteristics calculated by the respective calibration models are preferably determined and output, e.g., for further processing.

Analogously, the device summarized above thus includes at least one additional calibration model which is established on the basis of additional reference samples and which performs an additional calculation of the characteristics. A comparator arranged downstream from the calibration models determines and outputs the deviations between the characteristics calculated by the respective calibration models.

Double or multiple calculation of the characteristics using independent calibration models and the determination of the deviations between the calculated characteristics improve the reliability of the measurements and their robustness against the influences of unnoticed errors. Since the established deviations are available together with the calculated characteristics, the user is able to evaluate the quality of the measurement for each sample. In particular, by monitoring whether the determined deviations exceed a predefined threshold, it becomes possible to determine when the measuring error becomes too large. The measuring device according to the invention preferably can do this automatically during routine operation, so that it can also be used in otherwise unmonitored on-line operation. The need for regular check measurements is thus eliminated, and recalibration is necessary only if there is an automatically detected and reported exceeding of the threshold.

The additional calibration and computation effort required due to the at least one additional calibration model is not significant and corresponds to the number and selection of the samples used for calibration. The possible objection that by combining the reference samples used for the independent calibration models one could establish a single, more comprehensive calibration model and achieve a comparable improvement in the measuring behavior is accurate only in especially favorable cases, since the distribution of the reference samples must be carefully selected from the standpoint of uniform coverage of the measuring range. Furthermore, the possibility afforded by the invention of detecting simply and automatically any change relative to the calibration conditions would be lost.

There are different options to select the reference samples for establishing the calibration model and the additional reference samples for establishing the additional calibration model. It is useful if the reference samples and the additional reference samples, respectively, cover unequally large variation ranges of the characteristics to be determined in the samples. For instance, the one calibration model can be configured to cover a relatively large variation range with naturally selected reference samples, while the additional calibration model is established over a relatively narrow variation range using specially prepared samples. The one calibration model then calculates the characteristics in the larger variation range with relatively low resolution, while the additional calibration model calculates the characteristics in the narrower range with the higher resolution. A high robustness of the measurement is achieved in the narrower coverage range of the two calibration models, while a still useful measurement result is obtained in the broad range.

Furthermore, the calibration models can be established with reference samples or additional reference samples under slightly different boundary conditions, or with reference samples and additional reference samples taken at different times. Of course, the calibration models can be based not only on different reference samples but also on partially identical reference samples. The way the additional calibration models, whose scope of validity must of course intersect in the normal measuring range, are selected offers the possibility of taking into account any deviations that have to be expected based on experience, or of including any changes in samples that were recorded with an additional calibration, even while preserving the earlier experiences. In this manner, the measuring device can be incrementally adapted to changes, or a new calibration can be tested for its reliability in the measurement operations and can be improved incrementally. When a calibration is produced, the selection of previously determined spectral data of samples of a known composition is a step that is varied repeatedly and optimized in any case, so that the additional calibration models can be established without significant further effort.

A selection unit arranged downstream from the calibration models makes it possible, based on sample-specific and/or measurement situation-specific criteria, e.g., temperature or sample consistency, to select the most reliable among the characteristics calculated by the various calibration models. This makes it possible, for instance, to take into account foreseeable external influences by continuing to use the calculated characteristics for which the calibration conditions best correspond to the influence, without having to change the calibration itself.

BRIEF DESCRIPTION OF THE DRAWINGS

For the further description of the invention, reference is made to the drawing, which shows an exemplary embodiment of the inventive measuring device in a simplified block diagram.

DETAILED DESCRIPTION OF THE PREFERRED EMBODIMENTS

A sample 1 is subjected to spectral analysis in a spectrometer 2. To this end, the polychromatic light 3 of a radiation source 4, e.g., a halogen lamp, is supplied to a monochromator 5. The monochromator 5 depicted is an acousto-optic tunable filter (AOTF) whose optical properties are controlled by pinpointed excitation with ultrasonic waves, so that monochromatic radiation modes 6 with high wavelength accuracy in the near infrared range (NIR) are generated from the polychromatic light 3. The monochromatic light 6 is directed to a measuring cell 7 where it interacts with the sample 1. This causes the molecules of the sample 1 to vibrate in accordance with their structure and to exhibit typical energy absorptions. The light 8 transmitted or reflected by the sample 1 reaches a detector 9, which detects the energy absorption values and provides them as spectral data 10 on the output side.

Characteristics 12 of the sample 1, e.g., a certain molecule concentration, which are to be determined from spectral data 10, are calculated in a calibration model 11. To generate the calibration model 11, first spectral data 10' and characteristics 12', which are either known or established via reference analysis, are determined from selected or specially prepared reference samples 1'. Using a chemometric method, weighting functions are calculated in the form of a calibration matrix 13, and are applied to the spectral data 10' or 10 to yield, except for a certain error value, the characteristics 12' or 12.

In practice, it often occurs that some influences fail to be included when the calibration model 11 is established, e.g., due to the selection of the reference samples 1' or due to the external circumstances of the calibration. This can lead to increased measuring errors during operation. To be able to detect such measuring errors and identify the sample 1 involved early in the process, an additional calibration model 14 is provided, which is independent of the calibration model 11 and is established on the basis of reference samples 1" under slightly changed boundary conditions.

The two calibration models 11 and 14 are depicted here as separate circuit blocks to show their independence. In practice, however, the associated calibration matrices 13, 15 can be combined into a single matrix in which the input and output quantities can occur two or more times. The characteristics 16, calculated by the additional calibration model 14 from the spectral data 10 of the sample 1 during operation of the measuring device are compared in a comparator 17 with the characteristics 12 calculated by the calibration model 11. If the deviation between the calculated characteristics 12 and 16 exceeds a predetermined threshold, the comparator 17 generates a warning 18, which signals an excessively large measuring error.

As indicated by the dashed lines, a selection unit 19 can be arranged downstream from calibration models 11 and 14. Based on predetermined criteria 20, e.g., temperature or sample consistency, this selection unit 19 decides which of the calculated characteristics 12, 16 are the most reliable and outputs those as the result 21 of the measurement.

The above description of the preferred embodiments has been given by way of example. From the disclosure given, those skilled in the art will not only understand the present invention and its attendant advantages, but will also find apparent various changes and modifications to the methods and structures disclosed. It is sought, therefore, to cover all such changes and modifications as fall within the spirit and scope of the invention, as defined by the appended claims, and equivalents thereof.

What is claimed is:

1. Method for measuring characteristics of a sample by spectral analysis, comprising:

calculating the characteristics from spectral data obtained from the spectral analysis using a calibration model that has been established on the basis of reference samples;

performing an additional calculation of the characteristics of the sample based on the same spectral data using at least one additional calibration model that has been established on the basis of additional reference samples; and determining and outputting deviations between the characteristics calculated by the respective calibration models, to permit an evaluation of the quality of the measurement.

2. Method as claimed in claim 1, wherein the deviations are monitored for exceeding a predefined threshold.

3. Method as claimed in claim 1, wherein the reference samples and the additional reference samples each cover differently sized variation ranges of the characteristics.

4. Method as claimed in claim 1, wherein the calibration model and the additional calibration model are established, respectively, with the reference samples and the additional reference samples under slightly different boundary conditions.

5. Method as claimed in claim 1, wherein the calibration model and the additional calibration model are established with reference samples and additional reference samples obtained from different points in time.

6. Method as claimed in claim 1, wherein the characteristics calculated by one of the calibration models are selected based on at least one of sample-specific and measurement-situation-specific criteria.

7. Device for measuring characteristics of a sample comprising:

a spectrometer for spectral analysis of the sample;

a calibration model that has been established on the basis of reference samples and that calculates the characteristics from spectral data supplied by said spectrometer;

at least one additional calibration model that has been established on the basis of additional reference samples and that performs an additional calculation of the characteristics; and a comparator arranged downstream from said calibration models, which determines deviations between the characteristics calculated by said respective calibration models.

8. Device as claimed in claim 7, wherein said comparator checks whether the deviations exceed a predetermined threshold.

9. Device as claimed in claim 7, further comprising a selection unit arranged downstream from said calibration models, which selects the characteristics calculated by one of said calibration models based on at least one of sample-specific and measurement-situation-specific criteria that are supplied to said selection unit.

10. A method for measuring at least one characteristic of a sample by spectral analysis, comprising:

obtaining spectral data from a spectral analysis of the sample;

performing a first calculation of the characteristic of the sample from the spectral data obtained using a first calibration model that has been established on the basis of reference samples;

performing an additional calculation of the characteristic of the sample from the same spectral data using at least one different calibration model that has been established on the basis of at least partly differing reference samples; and comparing the characteristics calculated, respectively, by the first calibration model and the different calibration model.

11. The method as claimed in claim 10, further comprising outputting a signal if said comparing reveals a deviation in the respectively calculated characteristics that exceeds a predetermined threshold.

12. The method as claimed in claim 10, wherein the reference samples and the differing reference samples differ in extent of sample variation.

13. The method as claimed in claim 10, wherein the first calibration model and the different calibration model are established, respectively, with the reference samples and the differing reference samples under mutually different boundary conditions.

14. The method as claimed in claim 10, wherein the first calibration model and the different calibration model are established, respectively, with the reference samples and the differing reference samples taken from mutually different points in time.

15. The method as claimed in claim 10, further comprising selecting one of the respectively calculated characteristics in accordance with said comparing and at least one selection criterion.

16. A system for measuring at least one characteristic of a sample, comprising:

a spectrometer configured to output spectral data for the sample;

a first calibration model established on the basis of reference samples and configured to calculate the characteristic from the spectral data;

at least one additional calibration model established on the basis of at least partly differing reference samples and configured to calculate the characteristics from the spectral data; and a unit having inputs for the calculated characteristics of said first and said second calibration models and configured to output a comparison result of the calculated characteristics.

17. The system as claimed in claim 16, wherein the comparison result is a signal indicating a deviation in the calculated characteristics greater than a predetermined value.

18. The system as claimed in claim 16, wherein the comparison result is one of the calculated characteristics selected by said unit in accordance with a selection criterion.

* * * * *